United States Patent [19]

Cygielski

[11] Patent Number: 4,687,467
[45] Date of Patent: Aug. 18, 1987

[54] ONE-TIME USE MEDICAL SYRINGE INVENTION

[75] Inventor: Bozena Cygielski, Chicago, Ill.

[73] Assignee: C.T.F. Research Company, Chicago, Ill.

[21] Appl. No.: 872,934

[22] Filed: Jun. 11, 1986

[51] Int. Cl.⁴ .............................................. A61M 5/00
[52] U.S. Cl. .................................................... 604/110
[58] Field of Search ................ 604/110, 111, 218, 187

[56]  References Cited
FOREIGN PATENT DOCUMENTS 2298340  8/1976  France .................................. 604/110

*Primary Examiner*—John D. Yasko

*Attorney, Agent, or Firm*—Senniger, Powers, Leavitt and Roedel

[57]  ABSTRACT

Medical care device for only one-time use as a medical syringe for injection with destroyable piston after single use. Destruction of a syringe piston will occur after one-time use by cutting out a hole in the center of the front wall of the piston. In the very last moment of the injection stroke, the piston is pushed against the very sharp cylindrical cutting edge of the rear end of the tubular needle, which protrudes to the inside of the syringe cylinder for this purpose. With such a punctured piston it will be impossible to create a vacuum suction effect which is necessary to introduce any medication or liquid into the syringe cylinder for a second use. Simply put, nobody will be able to use this kind of syringe twice.

14 Claims, 4 Drawing Figures

ONE-TIME USE MEDICAL SYRINGE INVENTION

FIELD OF THE INVENTION

The present Invention generally relates to medical devices and its main function is to provide health care and medical care in such a safe manner which will eliminate any possible mistakes, misuse, use not related to medical use, and eliminate the possibility of infecting the patient or any other person by re-use.

DESCRIPTION OF THE PRIOR ART

In recent years, there has been a substantial increase in the use of individually sterilized, individually packaged so-called one-time use medical syringes. They gained popularity and the appreciation of medical personnel and also generally decreased the possibility of infecting an injected patient with germs or viruses that sometimes survived the sterilization process, a situation which occurred when multiple use syringes were sterilized after each use.

So-called one-time use medical syringes, presently dominating today's market, also have many other well-known advantages and disadvantages. The greatest disadvantage is that none of the presently used medical syringes, mistakenly called one-time use syringes, has the capability of destroying itself after a single use in an absolutely safe and sure manner so that they may not be mistakenly re-used by medical personnel or intentionally by others including non-professional persons or narcotics users.

In reality, mistakenly called one-time use syringes may be repeatedly used, beyond the control of medical personnel thus creating grave danger for people.

The present Invention does not have these disadvantages and its presented embodiment surely is adequate to the title—"The One-Time Use Medical Syringe for Injection with Destroyable Piston after Single Use". Nobody will be able to use it twice.

SUMMARY OF THE PRESENT INVENTION

The object of the present Invention called "The One-Time Use Medical Syringe for Injection with Destroyable Piston after Single Use" is a medical device for very wide medical care treatment. The One-Time Use Medical Syringe for Injection with Destroyable Piston after Single Use, will be usable one time, and will not be able to be used twice. In order to achieve this effect, the tubular needle rear end of a syringe will protrude to the inside of a syringe cylinder, and will have a very sharp cylindrical cutting edge. Nearing the end of the injection stroke, an opening hole in the center of the working surface of a specially formed flexible piston will automatically be cut out by the cutting edge which will protrude inside the syringe cylinder. It will be impossible to create a vacuum suction effect with such a punctured piston for introducing any other medication or liquid into the syringe cylinder for second time use.

The Invention consists of several novel features which are hereinafter set forth and are particularly defined by claims at the conclusion hereof.

DESCRIPTION OF THE PREFERRED EMBODIMENT

Figure 1:
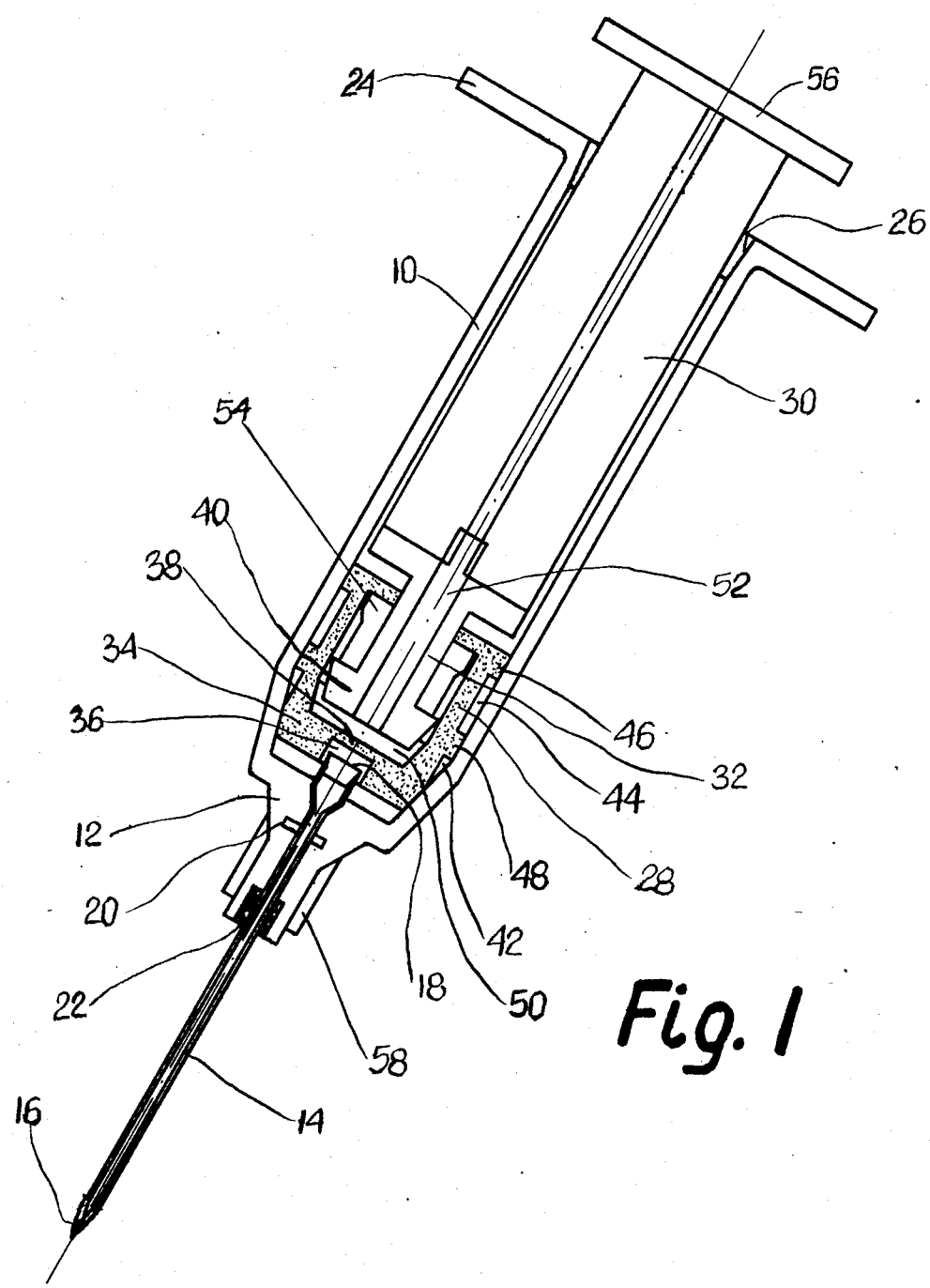
FIG. 1—is the enlarged cross section through the syringe in a ready to use condition.
Figure 2:
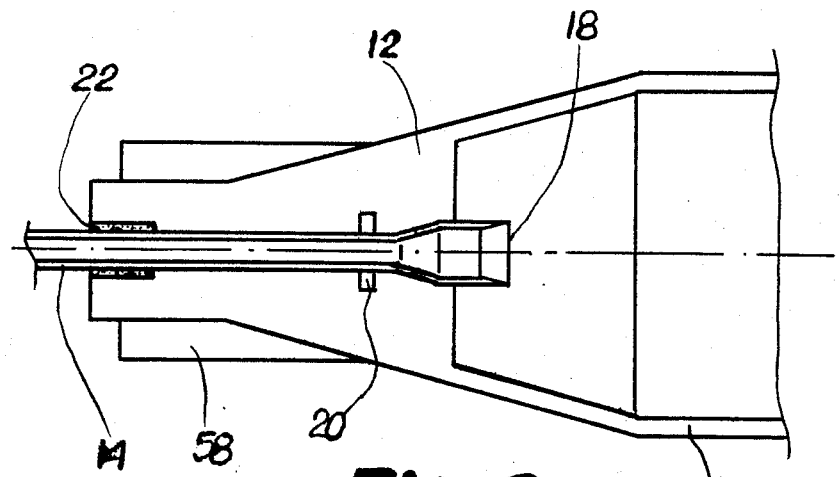
FIG. 2—is the enlarged partial cross section of the needle and syringe cylinder attachment.
Figure 3:
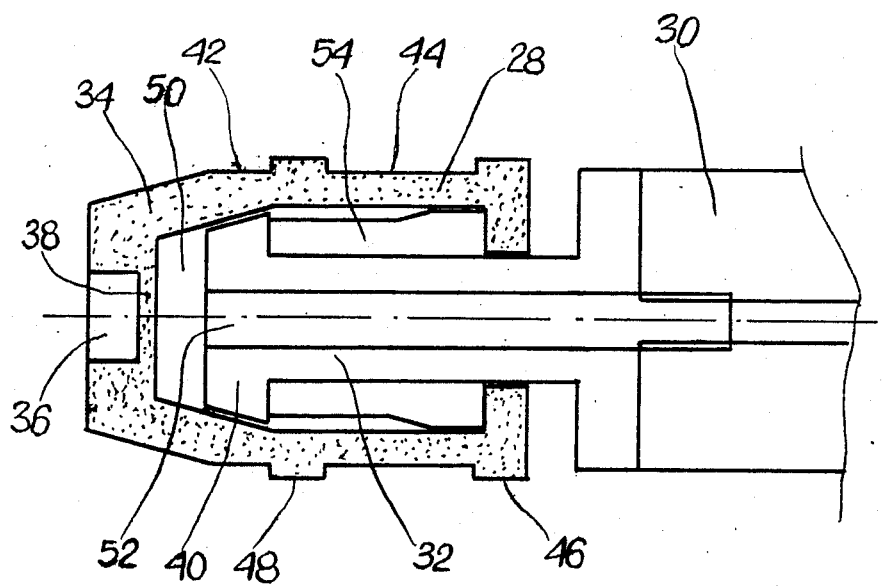
FIG. 3—is the enlarged partial cross section of the piston and syringe pushing rod attachment.

Referring now to the drawings, and more particularly to FIG 1, and in more enlarged detail in FIG. 2 and FIG. 3, the preferred embodiment of the present invention consists of circular syringe cylinder 10, which has the specially formed tubelike needle 14 molded into front section 12 of the syringe cylinder 10. Needle 14 has a specially sharpened front end 16 for easy penetration of the skin or muscles. The rear end of needle 14 has been formed by expanding or flaring the needle tube material, or otherwise attaching a slightly bigger tube having a very sharp cylindrical cutting edge 18, which protrudes inside of syringe cylinder 10. Needle 14, in the portion being molded inside front section 12, of cylinder 10, also has a small flange 20, which will secure needle 14 in the front end of cylindrical syringe body 10 firmly, and will protect needle 14 against being pulled out of its joint.

To assure a leak free joint of needle 14 to the front end of cylinder 12, needle 14 may also be additionally covered with a thin layer of special resin glue 22, which will seal this joint completely. At the rear end of cylinder 10 is formed a rectangular flange 24 and chamfered inner surface 26 to facilitate the movement of a piston generally designated 28 inside cylinder 10.

FIG 3 shows a new type of flexible piston 28 which is attached by snapping it on front end 32 of pushing rod 30. Piston 28 has front end 34 shaped similar to the front end of the inner cylindrical surface of syringe cylinder 10.

The sharp cylindrical cutting edge 18 of needle 14 protrudes inside of syringe cylindrical body 10 and will be shielded and protected inside concave cavity 36 of piston 28.

Bottom wall 38 of piston cavity 36 has enough thickness to allow cutting an opening through it easily when piston 28 is pushed further against sharp cylindrical edge 18 of needle 14. A front disc 40 included in rod 30 has a front flat surface which provides a cutting support surface for the edge 18 at the end of the injection stroke.

Flexible piston material will deform when an opening hole 60 in bottom wall 38 is cut by edge 18 against disc 40 in order to destroy the piston.

To help the piston material deform at the time the opening is cut, small take offs 42 and 44 are formed on the outside of piston body 28 adjacent two sealing rings 46 and 48 which are slightly bigger than the inside diameter of syringe cylinder 10.

During the injection stroke of piston 28, the conical shape of front disc 40, tends to expand the piston material to the outside, and by doing that, increase the sealing effect between piston 28 and syringe cylinder 10. Attachment of piston 28 to syringe push rod 30 is accomplished by forcibly introducing front end 32 of pushing rod 30 into inner chamber 50 of piston body 28.

Figure 4:
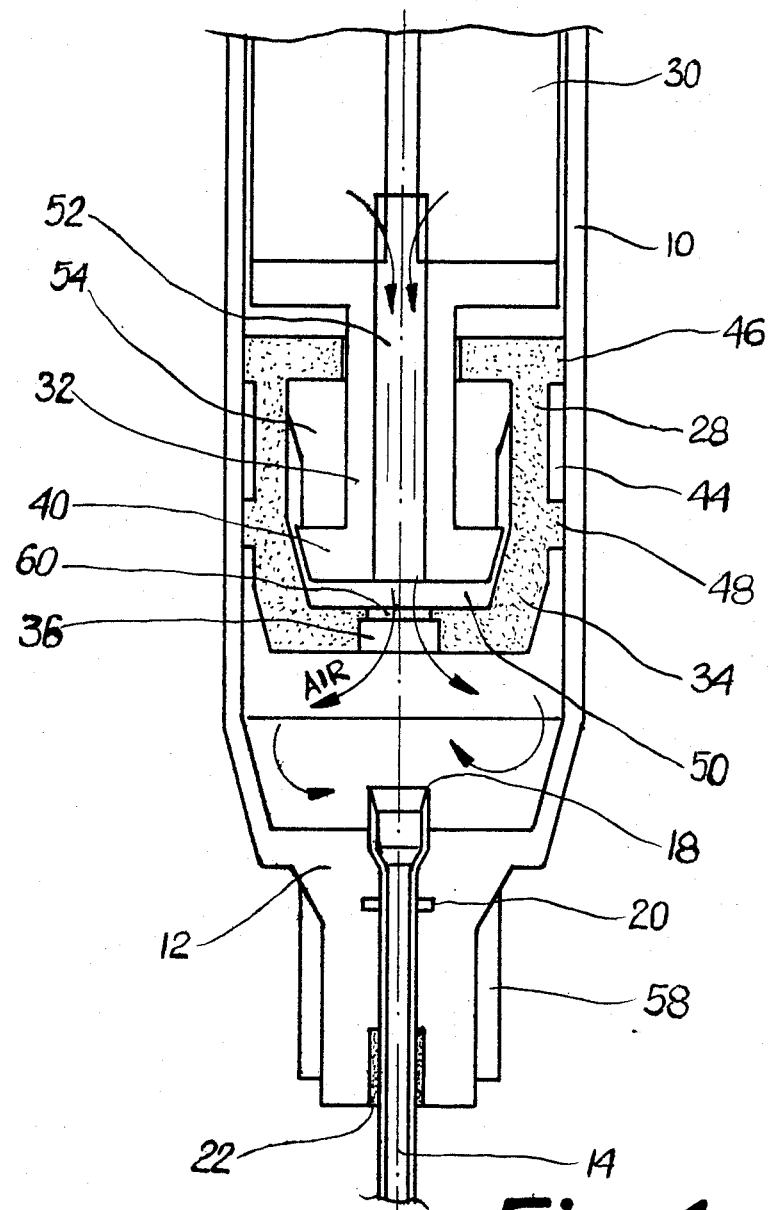
FIG. 4—is the enlarged partial cross section the syringe showing the piston and cylinder after an opening hole has been punctured in the piston.

In the center of the flat surface of front disc 40, there is cylindrical opening 52 slightly smaller than sharp cylindrical cutting edge 18 on needle 14 to allow the unobstructed flow of air through piston 28 from and to inner chamber 50 after the center opening hole 60 in piston bottom wall 38 is cut out, as illustrated by arrows representing flowing air in FIG 4.

On the outside of front end 32 of pushing rod 30, at least four reinforcing ribs 54 are formed around which piston body 28 also will be centered.

A flat circular disc 56 is located on top of the rear end of pushing rod 30 and is where the pushing force of the thumb is applied. Guiding ribs 58 are formed on the outside of the reduced cylindrical portion of the front end of syringe cylinder 10, and allow a protective cover for tubular needle 14 to snap on and be positioned and secured to the cylinder 10.

For the purpose of clarity the above mentioned protective cover is not shown in the drawing. It is also not illustrated on the drawings since it is obvious that on the outside surface of syringe cylinder 10, there will be an appropriate scale permanently marked showing the capacity of inner cylinder 10, and by that, allowing control of the amount of the medication being introduced inside syringe cylinder 10.

It will be apparent that various small changes may be made in the form of each component thereof without departing from the spirit and scope of the present invention.

Having described my invention, what I claim as new and desire to secure by letters patent is:

I claim:

1. A medical injection syringe comprising:
   a cylinder having an open end and a closed end and a cutting edge protruding into the interior of the cylinder at the closed end;
   a hollow needle mounted in the closed end of the cylinder in communication with the interior of the cylinder;
   a piston adapted to fit in the interior of the cylinder through the open end thereof and in sealing engagement with the cylinder for forcing fluid through the needle as the piston is pushed towards the closed end of the cylinder, the piston having a piston surface facing the cutting edge as the piston approaches the closed end of the cylinder;
   means surrounding the cutting edge for protecting the piston surface from being cut when the piston approaches the closed end of the cylinder; and
   pushing means for forcing the piston toward the closed end of the cylinder so as to force the fluid out the needle and such that when the piston engages the cutting edge, an opening hole is cut in the piston surface.

2. The syringe as set forth in claim 1 wherein the cutting edge is formed on the needle at an end in communication with the interior of the cylinder.

3. The syringe as set forth in claim 1 wherein the piston is made of silicone rubber and the pushing means includes a support surface behind the piston surface as the piston nears the closed end of the cylinder so that the piston surface is supported when the cutting edge cuts an opening hole.

4. The syringe as set forth in claim 3 wherein the protecting means has a circularly shaped opening into which the cutting edge can protrude and the cutting edge is cylindrically shaped such that the opening hole cut in the piston surface is substantially circular.

5. The syringe as set forth in claim 4 wherein the support surface includes a disc shaped member.

6. The syringe as set forth in claim 1 wherein the pushing means has an opening extending from a side near the piston to an outlet side toward the open end of the cylinder such that when the opening hole is cut air easily passes freely from the closed end of the cylinder to the open end.

7. The syringe as set forth in claim 6 wherein the cutting edge is cylindrically shaped and the opening is cylindrically shaped smaller in diameter than the cutting edge.

8. A medical injection syringe comprising:
   a cylinder having an open end and a closed end and a cutting edge protruding into the interior of the cylinder at the closed end;
   a hollow needle mounted in the closed end of the cylinder in communication with the interior of the cylinder;
   a piston adapted to fit in the interior of the cylinder through the open end thereof and in sealing engagement with the cylinder for forcing fluid through the needle as the piston is pushed towards the closed end of the cylinder, the piston having a cavity formed in the piston surface facing the cutting edge into which the cutting edge protrudes as the piston approaches the closed end of the cylinder; and
   pushing means for forcing the piston toward the closed end of the cylinder so as to force the fluid out the needle and such that when the piston engages the cutting edge, an opening hole is cut in the piston within the cavity formed therein.

9. The syringe as set forth in claim 8 wherein the cutting edge is formed on the needle at an end in communication with the interior of the cylinder.

10. The syringe as set forth in claim 8 wherein the piston is made of silicone rubber and the pushing means includes a support surface behind the cavity as the piston nears the closed end of the cylinder so that the cavity is supported when the cutting edge cuts an opening hole.

11. The syringe as set forth in claim 10 wherein the cavity is cylindrically shaped and the cutting edge is cylindrically shaped such that the opening hole cut in the cavity is substantially circular.

12. The syringe as set forth in claim 11 wherein the support surface includes a disc shaped member.

13. The syringe as set forth in claim 8 wherein the pushing means has an opening extending from a side near the piston to an outlet side toward the open end of the cylinder such that when the opening hole is cut air easily passes freely from the closed end of the cylinder to the open end.

14. The syringe as set forth in claim 13 wherein the cutting edge is cylindrically shaped and the opening is cylindrically shaped smaller in diameter than the cutting edge.

* * * * *